United States Patent [19]
Ueda et al.

[11] Patent Number: 4,628,740
[45] Date of Patent: Dec. 16, 1986

[54] PRESSURE SENSOR

[75] Inventors: Toshitsugu Ueda; Fusao Kohsaka; Yoshinobu Sugihara, all of Tokyo, Japan

[73] Assignee: Yokogawa Hokushin Electric Corporation, Tokyo, Japan

[21] Appl. No.: 785,909

[22] Filed: Oct. 9, 1985

[51] Int. Cl.$^4$ .......................... G01L 9/04; G01L 9/12; G01L 13/06
[52] U.S. Cl. ........................................ 73/705; 73/753; 250/231 P; 338/4
[58] Field of Search ........... 73/700, 705, 726, DIG. 4, 73/720, 753, 754, 30; 338/4; 374/201, 202; 250/231 P

[56] References Cited

U.S. PATENT DOCUMENTS 4,545,255 10/1985 Pugnaire .............................. 73/726
4,570,498 2/1986 Okayama .............................. 73/726

Primary Examiner—Donald O. Woodiel
Attorney, Agent, or Firm—Moonray Kojima

[57] ABSTRACT

A pressure sensor which detects delicate changes in pressure as small as 0.01 μm water column by detecting displacement or torque in a movable plate. The sensor comprises a fixed plate in which slits are formed, a movable plate on which pressure to be measured is impressed, a supporting member which supports the movable plate at two points on a straight line passing through its center of gravity so as to enable the movable plate to rotate thereabout, and a detecting means for detecting displacement or torque in the movable plate. The different pressures act on the movable plate to cause the rotation thereof and the displacement or torque so that such displacement corresponds to the pressure difference.

12 Claims, 17 Drawing Figures

FIG.6
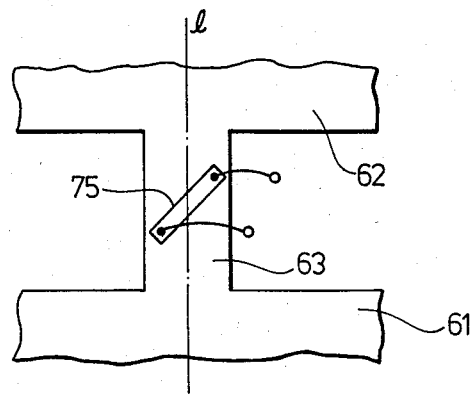
FIG.7(a)    FIG.7(b)
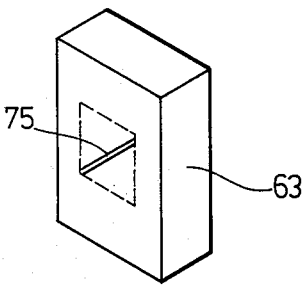 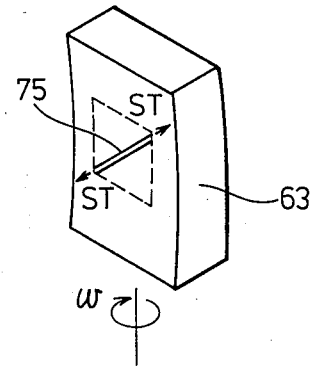

PRESSURE SENSOR

BACKGROUND OF THE INVENTION

1. Field of Invention

This invention relates to a pressure sensor which detects changes in pressure as displacement or torque in a movable plate; and more particularly, to a pressure sensor capable of effecting measurement of delicate changes in pressure, for example as small as that of a 0.01 μm water column. The invention can be used to detect infrared rays which can cause pressure changes in a chamber through which the rays are directed.

2. Description of the Prior Art

Condenser microphones are well known as pressure sensors which are capable of measuring small pressures. The condenser microphone generally comprises a metal film which receives the pressure and a fixed electrode which is disposed opposite the metal film. It detects the displacement of the metal film caused by the pressure, such displacement being defined as a change in electrostatic capacities between the metal film and the fixed electrode.

However, the prior devices have a disadvantage in that they are impossible of attaining favorable characteristics because of the non-uniformity of the sensitivity of detection, and in that to attain some measure of uniformity, the metal film is stretched so as to apply tension to the entire surface which causes other problems. Moreover, the sensitivity of detection is high under those conditions, but, on the other hand, such prior devices tend to be then influenced by vibration noises and by changes in position or posture. Other deficiencies are known to exist and hence these prior device leave much to be improved upon.

SUMMARY OF THE INVENTION.

Accordingly, an object of the invention is to overcome the aforementioned and other deficiencies and disadvantages of the prior art.

Another object is to provide a highly sensitive pressure sensor which is of simple construction and which has less tendency to be adversely influenced by vibration noises and by changes in position or posture.

The pressure sensor of the invention comprises a fixed plate comprising slits; a movable plate disposed opposite to the fixed plate and subjected to the pressure to be measured; a supporting member supporting the movable plate at two points on a straight line passing through the center of gravity thereof so as to enable the movable plate to rotate about the straight line; and a detecting means for detecting the displacement or torque in the movable plate. Different pressures on different parts of the movable plate cause the plate to rotate with the consequent displacement or torque on the movable plate being indicative of the pressure being measured. In one use of the pressure sensor, infrared rays are applied to a chamber to cause pressure change therein, which pressure change is applied to the pressure sensor, with consequent displacement of the movable plate. In this manner, the invention can also be used to measure the incident infrared rays.

BRIEF DESCRIPTION OF THE DRAWINGS

FIGS. 5, 6, 8 and 9 are block diagrams depicting detecting means for detecting the rotational displacement or torque of the movable plate.

FIGS. 7(A) and 7(B) are perspective view depicting the motion shown in FIG. 6.

DETAILED DESCRIPTION OF PREFERRED EMBODIMENTS

Figure 1:
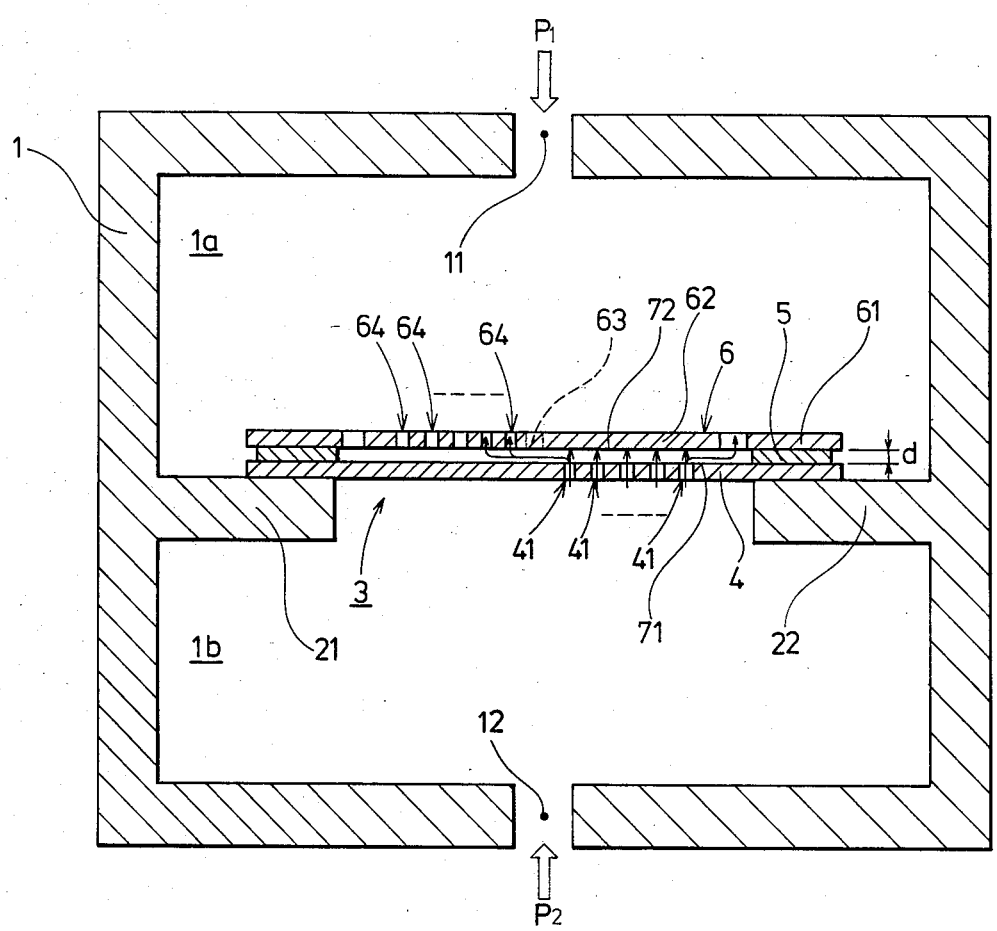
FIG. 1 is a sectional view depicting the structure of an illustrative embodiment of the invention.
Figure 2:
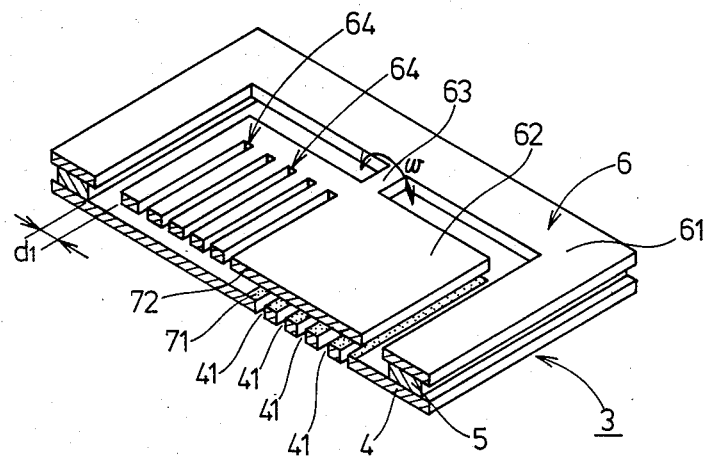
FIG. 2 is a perspective view depicting, partly in section, a principal portion of the embodiment of FIG. 1.
Figure 3:
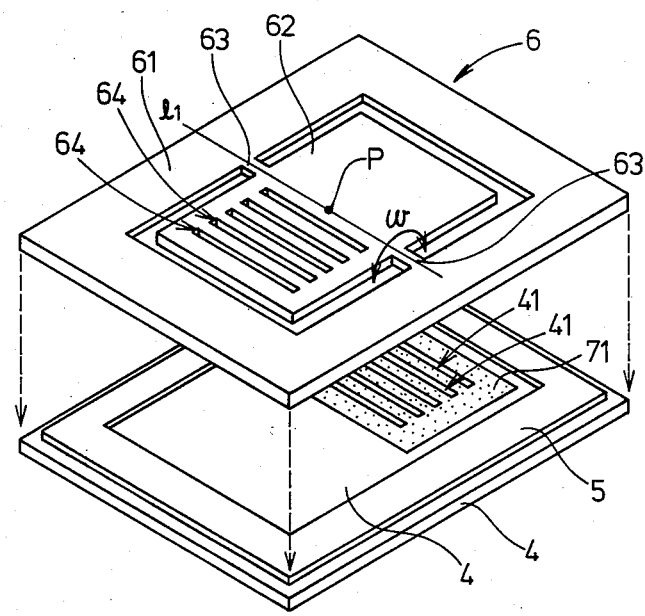
FIG. 3 is a perspective view depicting an assembly block diagram of the principal portion of FIG. 2.

Turning now to FIGS. 1, 2 and 3, an illustrative embodiment is depicted wherein differential pressure between pressure P1 and pressure P2 is detected. A container 1 having partition walls 21, 22 bipartitely partition the inside thereof. Pressures P1,P2 to be measured are introduced through pressure introduction holes 11,12 into each of chambers 1a, 1b which are formed and partitioned by partition walls 21,22. It is assumed that, when the pressures are introduced, both P1 and P2 become pulsating. A pressure detecting unit 3 which is a feature of the invention, comprises a fixed plate 4 and a movable member 6. Fixed plate 4 is fixed on partition walls 21,22. Movable member 6 is disposed opposite to fixed plate 4 through the medium of a spacer 5. A minute interstice d is formed between fixed plate 4 and movable member 6. It is to be noted that a deposit formed on fixed plate 4 may serve as spacer 5, thereby to provide the minute interstice d.

Fixed plate 4 is provided with a plurality of slits 41 (in this case, five slits are formed) which are designed for introducing the pressure from within chamber 1b. Movable member 6 comprises a frame 61 and a movable plate 62. Frame 61 supports movable member 6 through the intermediary of supporting embers 63. Movable plate 62 is disposed opposite to fixed plate 4. and is provided with a plurality of slits 64 (in this case, five slits are provided) which are disposed opposite to slits 41 of fixed plate 4. Supporting members 63, functioning as a spring, support movable plate 62 at two points on a straight line $l_1$ passing through the center of gravity P (as depicted in FIG. 3), of movable plate 62 so as to enable movable plate 62 to rotate.

In this embodiment, movable plate 62 comprises slits 64 only on the left side with respect to straight line $l_1$ (which is equivalent to a rotational axis) formed between supporting members 63.

An electrode plate 71 (see FIGS. 2,3) is provided on fixed plate 4. An electrode plate 72 (see FIG. 2) is provided on movable plate 62 opposite to electrode plate 71. These electrode plates 71, 72 constitute a detecting means for detecting the displacement in movable plate 62.

The operation of the embodiment is as follows. In a state wherein the pressure is not yet introduced from or through holes 11, 12 into chambers 1a and 1b (that is, the pressure within chamber 1a is equal to that within chamber 1b) movable plate 62 is undisturbed and the minute interstice d formed between fixed plate 4 and movable plate 62 is undisturbed.

Figure 4:
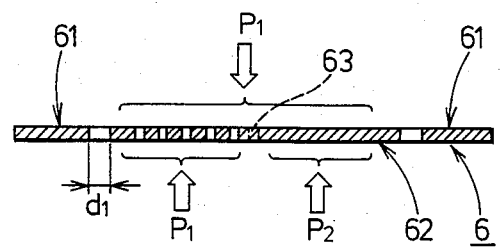
FIG. 4 is a front elevational view depicting the pressurized state of a movable plate.

When pressures P1,P2 are respectively introduced through holes 11,12 (with pressure P1 being assumed to be smaller than pressure P2), pressure P2 within chamber 1b is exerted through a plurality of slits 41 formed in fixed plate 4, as shown in FIG. 1 by arrow heads on the under surface of one side of plate 6 in which no slits are formed. Pressure P1 within chamber 1a is applied on the entire surface of movable plate 62. At the same time, pressure is exerted through slits 64 of movable plate 62 as shown in FIG. 1 by arrow heads on the under surface of the other side in which slits 64 of movable plate 62 are formed. FIG. 4 also shows a situation wherein movable plate 62 is pressurized in such state.

With this arrangement, pressure P1 acts on both the surface and the under surface on one side of movable plate 62 since slits 64 are formed therein and no torque is thus produced. On the other hand, pressure P1 is placed onthe surface thereof and pressure P2 is impressed on the under surface thereof with respect to the other side of movable plate 62 on which slits 64 are not provided. Thus, torque is created in proportion to the difference between P1 and P2. This torque acts on supporting members 63. Supporting members 63 function as springs and become torsional by action of the torque, as shown in FIGS. 2,3 by arrow head ω, so that movable plate 62 rotates to an angle which corresponds to the difference between P1 and P2.

Since fixed plate 4 and movable plate 62 are respectively provided with slits 41 and 64, and further, since movable plate 62 is separated from frame 61, the fluid (e.g. gas or liquid) existing within chambers 1a,1b leaks out via these slits. The fluid resistance caused at the respective portions is increased by decreasing the sizes of slits 41, 64, air gap d1 formed between movable plate 62 and frame 61 (see FIGS. 2,4) and interstice d formed between movable member 6 and fixed plate 4 (see FIG. 1), thereby making it possible to slope (i.e. rotate) movable plate 62 at an angle which corresponds to the difference between pressure P1 and P2.

The displacement (i.e. change in oblique angle) of movable plate 62 is deemed as a change in electrostatic capacities between electrodes plates 71,72. It is practicable to distinguish the difference between pressures P1 and P2 by measuring the variation in such electrostatic capacitances. Each of pressures P1 and P2 assumes pulsating properties. Where pressure P1 is greater than P2 movable plate 62 slants in the opposite direction to that shown in and described for the above embodiment.

In the above described embodiment, movable plate 62 is supported at two points along a straight line passing through the center of gravity thereof. The torque (or slope) in movable plate 62. which is created by the pressure difference is detected. On the other hand, the acceleration (i.e. the translation kinetic component) caused by gravity and outside vibration is not of sufficient torque force to rotate movable plate 62. Thus, advantageously, in the invention, it is possible to accurately measure the pressure without being subjected to adverse influenced due to vibration noises and changes in posture (i.e. as the position is affected by gravity).

Also, if the pressure to be measured pulsates at a predetermined frequency, and when a resonant frequency $f_o$ of the movable member (which is determined by inertia moment I and a spring constant K of supporting member 63) is made to coincide with the pulsating frequency of the pressure to be measured, it is feasible to improve the ratio S/N as well as enhancing the sensitivity of detection.

Namely, when the pulsating pressure is applied on movable plate 62, this movable plate vibrates (i.e rotational displacement) at a given amplitude in accordance with the pulsating pressure. The reason for this phenomenon is that the vibrational amplititude of the movable member increases Q-fold due to the resonance, if the resonant frequency $f_o$ of the movable member is made to coincide with the frequency of the pulsating pressure. Q is expressed by the following equation $$Q = I\omega_o/R \tag{1}$$

wherein R is the dampling resistance and $\omega_o$ is the angular frequency at a resonant time. $\omega_o$ is manifested by this equation $$\omega_o = K/I.$$

The resonant frequency $f_o$ of the movable member can be adjusted by varying the number of slits 64 of movable plate 62 and the construction thereof or the material of which it is made, and by varying spring constant K of supporting member 63. Moreover, damping resistance R , with respect to the resonance of movable plate 62, can also be adjusted by changing the size and number of slits which are formed in movable plate 62 and fixed plate 4 and by changing the distance of interstice d formed between movable member 6 and fixed plate 4.

In the above embodiment, the changes in electrostatic capacities between electrode plates 71,72 are detected, and correspond to the measurement of pressure These are provided on one side with respect to the rotational axis $l_1$ of movable plate 62. Thus, the rotational displacement of movable plate 62 caused by the torque acting on plate 62 about member 63, changes the capacitance between the plates 71,72.

Another arrangement is to provide electrode plates on either side with respect to the rotational axis of movable plate 62, and additional electrode plates on the side of fixed plate 4 such as to be disposed opposite to the previous electrode plates. With this 1 arrangement, the differences between electrostatic capacitances C1 and C2 between the respective electrode plates which are opposite to each other can be detected. In this case, the sensitivity of detection is doubled as compared with the above embodiment. With this arrangement, it is possible to subsantially effectively eliminate the adverse influences due to gravity and vibration.

The rotational displacement or torque in movable plate 62 can be detected using various means. FIGS. 5,6,7 and 9 depict illustrative detecting means for detecting the rotational displacement or torque in movable plate 62.

Figure 5:
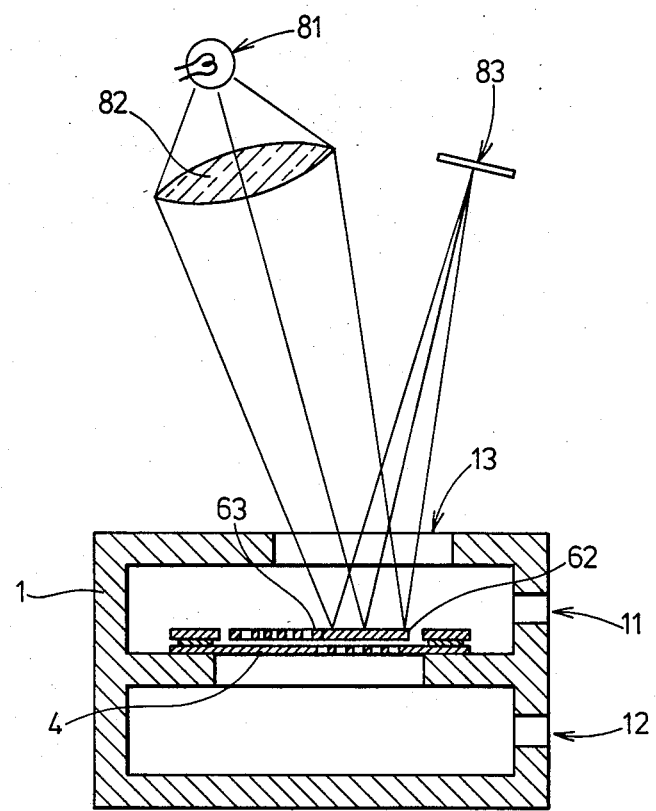

In the embodiment of FIG. 5, container 1 is provided with a window 13 designed for optical transmission. The surface of movable plate 62 is irradiated with light emitted from a lamp 81 and focussed through lens 82 and directed through window 13. With this step, the displacement of the reflected light which is concomitantly caused by the rotational displacement of movable plate 62, is detected by means of an optical receptor 83. The surface of movable plate 62 is arranged to reflect the light and lens 82 is positioned to focus the light after reflection by the surface of plate 62, at a certain point on optical receptor 83. Other focusing means can be used.

According to the embodiment of FIG. 5, since it is not necessary to lead an electrical signal, such as via a wire, or the like, into container 1, advantageously, the apparatus is simply in structure and has a high safety factor in preventing explosions, as electrical fixtures tend to cause in such devices of the prior art.

In the embodiment of FIG. 6, a strain gauge 75 is mounted on supporting member 63 of movable plate 62. A change in strain of the supporting member 63, which is caused by rotational displacement of movable plate 62, is detected as a change in resistance of strain gauge 75. The gauge 75 is preferably mounted on supporting member 63 at an angle of 45° with respect to the rotational axis $l_1$ thereof, for optimal effect, although other angular positions may be used.

When no torsion is created in support member 63 (that is when torque does not act on movable plate 62) strain gauge 75 is not subjected to strain (as shown in FIG. 7, line (A)) and no change in value of resistance is produced. As shown in FIG. 7, line (B), when torsion $\omega$ is created by rotation of movable plate 62, the torsion shown by arrow head ST is given to strain gauge 75, thereby varying the value of its resistance. This change in resistance is measured and corresponds to the pressure measured by the sensor.

Figure 8:
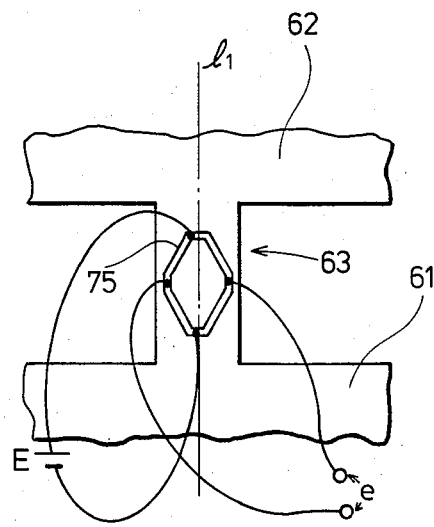

In the embodiment of FIG. 8, four strain gauges 75 are mounted on supporting member 63, each of which makes an angle of 45° with respect to the rotational axis $l_1$ thereof. These strain gauges 75 are connected to each other by using bridges. The power source ends of the bridges are further connected to a DC power source E in order to obtain a signal e transmitted from a voltage detecting end as an output voltage. Advantageously, this bridge type detecting arrangement has high sensitivity.

Figure 9:
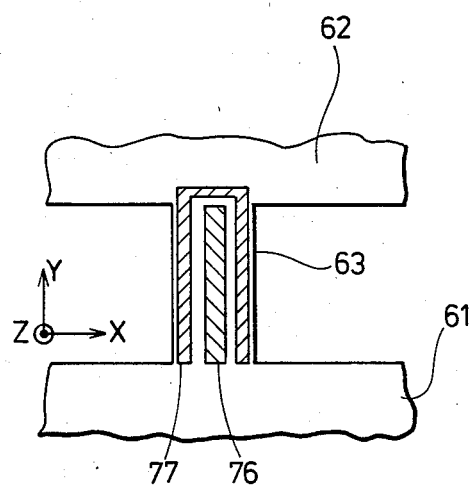

In the embodiment of FIG. 9, supporting member 63 comprises, or example, a rock crystal, which has piezoelectric effects. Electrodes 76,77 are disposed thereon opposite to each other as shown. A change in stress, which is produced in supporting member 63, is detected as a variation in electric charge between electrodes 76,77 by the piezoelectric effect.

Figure 10:
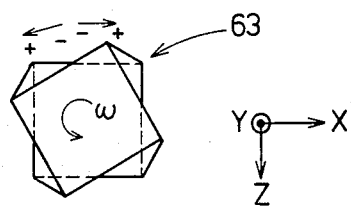
FIG. 10 is a pictorial view depicting the motion shown in FIG. 9.

If supporting member 63 is formed of a rock crystal, which has crystallographic axes in the directions indicated by arrow heads X,Y,Z, and when supporting member 63 becomes torsional, as shown in FIG. 10, electric charge is produced in the axial direction X. The polarity of this electric charge is reversed as shown in FIG. 10 because the direction of shearing strain becomes opposite when making a comparison between one direction +X and the other direction −X, on the basis of the torsional center. Thus, it is possible to detect at electrodes 76,77, the electric charge which is produced by supporting member 63 corresponding to the torsion created therein.

In FIGS. 9, 10, supporting member 63 comprises a piezoelectric material. It is, however, possible to form member 63 of other materials and then provide a piezoelectric material, such as PZT, thereon. With this arrangement, the stress or strain created in supporting member 63 can be similarly detected.

Figure 11:
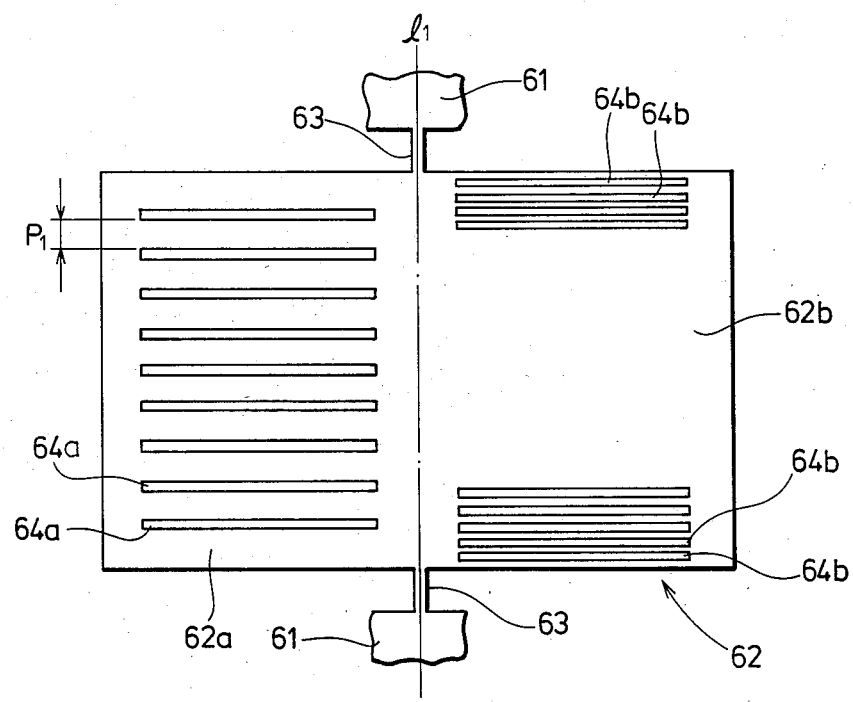
FIG. 11 is a plan view depicting a principal portion of another illustrative embodiment of the movable plate.
Figure 12:
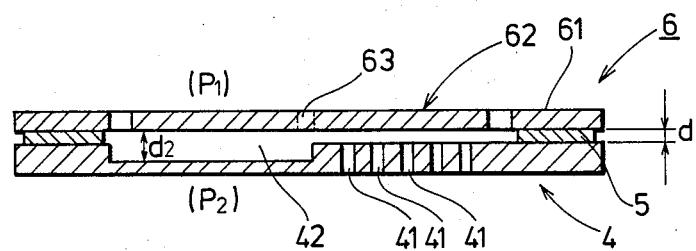
FIG. 12 is a sectional view depicting the principal portion of another movable part.

FIG. 11 and 12 depict another illustrative moving plate 62 wherein a plurality (in this case nine slits) of slits 64a are formed at a pitch P1 in movable plate 62 in such a way that these slits extend almost entirely over half the surface 62a on the left side with respect to axis $l_1$. On the other hand, slits 64b, which are the same in number and shape as slits 64a, are formed in the other half surface 62b on the right side thereof. These slits 64b are divided substantially in two parts and disposed at the upper and lower peripheral portions thereof, as depicted.

Since movable plate 62 is thus formed, rotational axis $l_1$ of movable plate 62 may be identical with the position of bilateral symmetry. Even if the configuration of slits 64a varies more or less, such variation can be compensated for on the side of slits 64b. Consequently, it is feasible to easily balance the right and left sides.

In this embodiment, slits 64a and 64b have such a configuration that each of them extends preferably at right angles to axis $l_1$. However, slits 64a and 64b may be so arranged as to extend parallel to or at other angles to the axis $l_1$.

In the embodiment of FIG. 12, movable plate 62 has no slit. Instead, a recessed portion 42 is formed on one side with respect to rotational axis $l_1$ of movable plate 62. An interstice d2 (d<d2) is thus formed in the recessed portion formed between fixed plate 4 and movable plate 62. According to this arrangement, the pressure within recessed portion 42 is P1 or almost equivalent to it. Thus, the torque which corresponds to the difference between P1 and P2 acts on movable plate 62 to cause torsion to rotate plate 62 about member 63 in the manner described.

Figure 13:
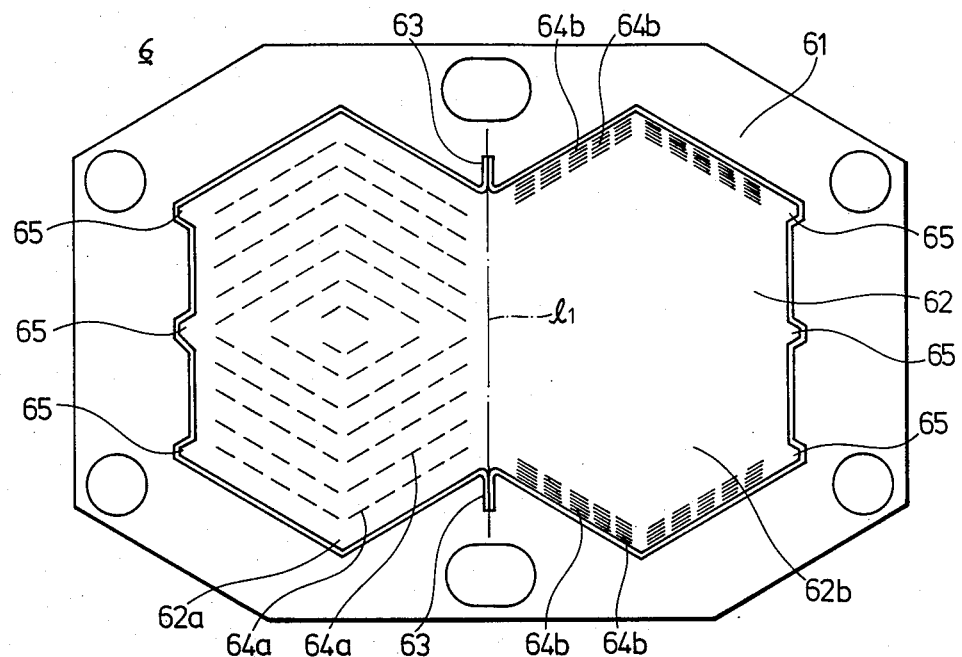
FIG. 13 is a plan view depicting a movable member comprising a material capable of effecting anisopropic etching.

FIG. 13 is a plan view depicting another illustrative embodiment, wherein movable member 6 comprises an Si substrate capable of effecting anisotropic etching or a rock crystal plate which is defined as a single crystal of glass or $SiO_2$. In this embodiment movable plate 62 is a multi-angular shape and comprises a half surface 62a on the left side and another half surface 62b on the right side, with respect to axis $l_1$, and disposed between supporting members 63 respectively. In addition, a plurality of slits 64a are entirely provided on half surface 62a. Slits 64b which are the same in number and shape as slits 64a, are provided at the upper and lower peripheral portions of the other half surface 62b. Also, projected portions 65 are provided at the respective pointed ends (the remotest portions from axis $l_1$) of movable plates 62a, 62b. These projected portions 65 serve as over range stoppers.

Figure 14:
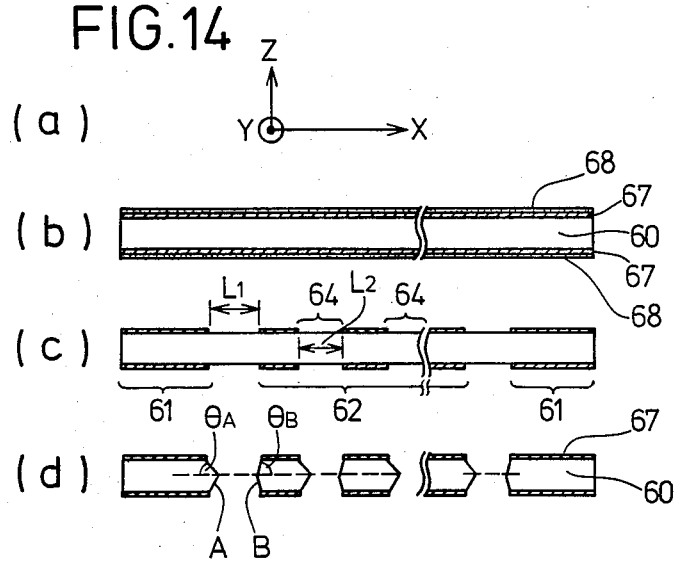
FIG. 14 depicts in lines (A) through (D) a brief process flow chart of an illustrative embodiment of a method for producing the movable member shown FIG. 13.

FIG. 14 depicts a brief process flow chart of an illustrative method of manufacturing the movable plate member shown in FIG. 13. In this embodiment, a Z plate made of $\alpha$ rock crystal is used as a substrate FIG. 14, line (A) illustrates each of the directions of an optical axis Z, a mechanical axis Y and an electrical axis X of a rock crystal substrate 60.

In a first step, a layer 67 comprising a masking material such as, for example, Cr, Ni or the like, is deposited, as shown in line (B), on either surface of the Z substrate 60, made of rock crystal, by sputtering or vapor deposition. Then, a resist layer 68 is deposited thereon, by, for example, coating.

Then, frame 61, movable plate 62, slits 64 and supporting member 63 (not shown in FIG. 14) are formed from the structure of line (B), at predetermined configurations by photolithography, as shown in line (C). In such a case, a spacing L1 between frame 61 and movable plate 64 and a width L2 of the slit 64 are individually made greater than predetermined dimensions.

In the next step, the rock crystal substrate 60 is etched by dipping in a rock crystal processing agent, such as for example, an aqueous solution of hydrofluoric acid, and substrate 60 is selectively removed as shown in line (D), thereby forming movable member 6 in the predetermined desired shape.

An etching process was used to take advantage of the different etching rates in different directions of the crystal. In relation to the rock crystal substrate 60, an etching velocity from the axial direction Z is several tens of times or more as fast as the etching velocity in regard to the crystalline surface A,B, as shown in line (D). In this case, an angle $\theta_A$ shown in line (D) is 30° and an angle $\theta_B$ is 80°. Thus, the etching process in the lateral direction is not developed any more. In the case of separating the rock crystal 60 (if it is to be removed), spacings L1,L2 between the patterns may be selected to be of a length Lo. The length Lo is obtained from the following equation $$Lo = \frac{t}{2} \cdot \tan(90 - \theta_A) + \tan(90 - \theta_B)$$

wherein t is the thickness of the rock crystal substrate 60.

In this case, the etching process is carried out concurrently on both side surfaces. Such etching process may, however, be effected at only one surface as desired. At this time, L1, L2 are selected to be more than double the length Lo.

There is an advantage in the above process wherein it is possible to form simultaneously a plurality of frames, movable plates, and slits with the simple operation just described. Moreover, this illustrative process involves forming an electrode plate on substrate 60 without requiring complex steps.

The method of the manufacturing of the movable member shown in FIG. 14 can be similarly applied to the fixed plate 4. This involves an arrangement wherein a material capable of effecting the anisotropic etching is used for the substrate.

Figure 15:
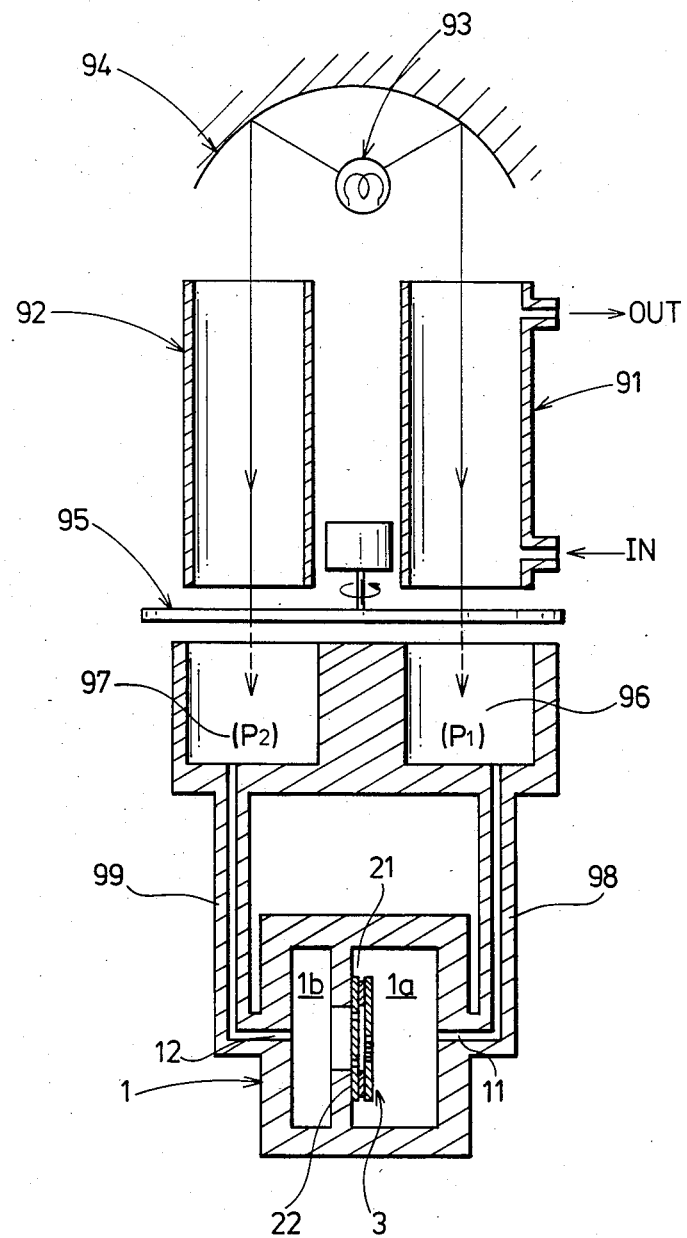
FIGS. 15 and 16 are sectional views depicting use of the invention in an infrared ray analyzer.

FIG. 15 is a sectional view depicting an infrared analyzer using the invention. The analyzer can analyze the density of a wide variety of gases by utilizing the absorption properties in the infrared ray wavelength region. The infrared ray analyzer investigates the density, and the like, of a gas to be measured, by a method wherein the gas to be measured is irradiated with a light flux of infrared rays emitted from a light source. The infrared rays which are passed through the gas to be measured is then applied to a chamber having a gas therein which expand by absorbing the infrared rays. Then, the pressure generated by this expansion within the chamber is measured by the pressure sensor.

In FIG. 15, the gas to be measured is introduced into measuring cell 91. A gas having a standard density, such as $N_2$ or the like, is encapsulated in a comparison cell 92. A light source 93 of infrared rays emits infrared rays which are reflected on a concave mirror 94 and then directed into measuring cell 91 and comparison cell 92. Measuring cell 91 is filled with gas to be measured, and the gas having the standard density is encapsulated in comparison cell 92, as described. A light chopper 95 is provided for chopping light at a regular period, which had priorly been penetrated through cells 91,92. The chopper 95 is disposed in the manner depicted so as to provide the chopped light to the chambers 96,97 which are disposed opposite cells 91,92. A suitable gas having the ability to swell by absorbing the energy of incident infrared rays, is encapsulated in these light receiving chambers 96,97. A pressure sensor 1 of the invention is provided to detect the difference between the pressures created within light receiving chambers 96,97. Pressures P1,P2 are imparted via conduit lines 98, 99 to pressure sensor 1. Pressure P1 corresponds to the density of the gas to be measured and pressure P2 similarly corresponds to the standard density of the gas. Advantageously, by the arrangement described, it is possible to stably measure the density of a gas to be measured without any adverse influence caused by atmospheric gas at the place whereat the analyzer is placed or caused by changes in position of the light source, or caused by moisture in the atmosphere.

Figure 16:
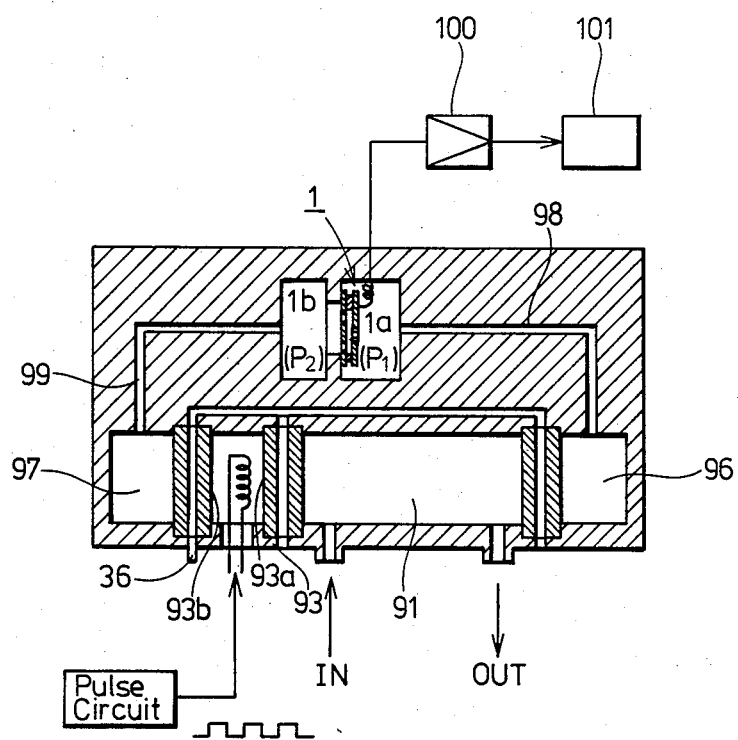

FIG. 16 is a sectional view showing another infrared ray analyzer adopting the pressure sensor of the invention. This embodiment does not use a comparison cell as done in the FIG. 15 embodient. Light source 93 of infrared rays, which is intermittently driven by a pulse circuit, emits light fluxes of intermittent infrared rays in two directions through the means of infrared ray transmission windows 93a, 93b. Light receiving chamber 96 receives light flux of infrared rays which has penetrated through window 93a and through the gas, which is to be measured, and which is within the measuring cell 91. On the other hand, light receiving chamber 97 directly receives the light flux of infrared rays which has passed through infrared ray transmission window 93b. A gas is encapsulaed into each of light receiving chambers 96,97 and has the ability to swell or expand when it absorbs incident infrared rays. Pressures P1,P2 correspond to the energy of the incident infrared rays produced in the respective chambers 96,97. P1 and P2 are impressed via conduit lines 98,99 on pressure sensor 1 whereat the difference between the pressures within the light receiving chambers 96,97 is detected, in the manner previously discussed. An output signal is generated by the pressure sensor 1 and is amplified by means of an amplifier 100 and is then outputted to be shown by an indicator 101.

The apparatus of this embodiment does not include a comparison cell which tends to change in properties with age. Thus, advantageously, with this embodiment, by removing from the optical path a component that might deteriorate with age, a more stable and reliable measurement has been attained. There is substantially no zero drift with this embodiment.

In each of the above embodiments, the pressure produced in chamber 96,97 is led into each of the respective chambers 1a, 1b of the pressure sensor 1. However, with other suitable devices, the infrared rays may be directed into chamber 1a, 1b, and suitable measurements made.

The foregoing description is illustrative of the principles of the invention. Numerous other modifications and extensions thereof would be apparent to the worker skilled in the art. All such modifications and extensions are to be considered to be within the spirit and scope of the invention.

What is claimed is:

1. A pressure sensor comprising
   a fixed plate comprising slits through which pressure is introduced;

a movable plate disposed opposite to said fixed plate and being subjected to a first pressure and a second pressure;

a supporting member rotatably supporting said movable plate at two points on a straight line passing through the center of gravity of said movable plate;

wherein said first pressure is applied on one surface of said movable plate and said second pressure is introduced through said slits in said fixed plate and is impressed on the other side of said movable plate, thereby to rotate said movable plate in accordance with the difference between said first pressure and said second pressure; and detecting means for detecting displacement or torque in said movable plate caused by said rotation of said movable plate, and for generating a signal indicative of said displacement or torque corresponding to said difference between said first pressure and said second pressure.

2. The sensor of claim 1, wherein said first pressure and said second pressure pulsate at a predetermined period; and wherein said movable plate has a resonant frequency determined by an inert moment of said movable plate and by a spring constant of said supporting member, said resonant frequency coinciding with said pulsating frequency of said first and second pressures.

3. The sensor of claim 1, wherein said movable plate has a plurality of slits formed in one half surface on a left side thereof with respect to said straight line, and said second pressure is applied on the other side of a right side thereof.

4. The sensor of claim 3, wherein said movable plate comprises a plurality of first slits formed substantially entirely over said first half surface on said left side, and a plurality of second slits of the same number and shape as said first slits, formed at upper and lower peripheral portions of said other half surface on said right side.

5. The sensor of claim 1, wherein said movable plate comprises projected portions provided at remotest portions from said straight line, said projected portions serving as over range stoppers.

6. The sensor of claim 1, wherein said fixed plate comprises a plurality of slits and a recessed portion, said slits being formed on one side with respect to said straight line, said recessed portion being formed on the other side thereof.

7. The sensor of claim 1, wherein said detecting means comprises electrode plates provided on said fixed plate and said movable plate and disposed opposite to each other; wherein said detecting means detects a change in electrostatic capacities between said electrode plates or a differential change in said electrostatic capacities, thereby generating a signal corresponding to said differential pressure.

8. The sensor of claim 1, wherein said detecting means comprises a strain gauge or a piezoelectroc element for detecting strain or stress created in said supporting member, said strain gauge or said piezoelectric element being mounted on said supporting member.

9. The sensor of claim 1, wherein said detecting means consists essentially of an optical means, said optical means comprises means for irradiating said movable plate with light and a light receiving element for receiving light reflected from said movable plate.

10. The sensor of claim 1, wherein said supporting member comprises a piezoelectric material, and wherein said detecting means comprises a pair of electrodes provided on said supporting member.

11. The sensor of claim 1, wherein at least said movable plate and said supporting member are formed by a single substrate of a material capable of effecting anisotropic etching, and wherein said movable plate and said supporting member are formed by photolithography and etching.

12. The sensor of claim 1, wherein said first pressure and said second pressure correspond to density of a gas having the ability to swell or expand by absorption of infrared rays.

* * * * *